(12) United States Patent
Woerner et al.

(10) Patent No.: US 9,856,280 B2
(45) Date of Patent: Jan. 2, 2018

(54) METHOD FOR PRODUCING AQUEOUS PREPARATIONS OF COMPLEXES OF PLATINUM GROUP METALS

(71) Applicant: Umicore AG & CO. KG, Hanau-Wolfgang (DE)

(72) Inventors: Eileen Woerner, Nidderau (DE); Ralf Karch, Kleinostheim (DE); Andreas Rivas-Nass, Schriesheim (DE); Angelino Doppiu, Seligenstadt (DE)

(73) Assignee: Umicore AG & Co., KG (DE)

( * ) Notice: Subject to any disclaimer, the term of this patent is extended or adjusted under 35 U.S.C. 154(b) by 20 days.

(21) Appl. No.: 14/650,903

(22) PCT Filed: Dec. 11, 2013

(86) PCT No.: PCT/EP2013/076263
§ 371 (c)(1),
(2) Date: Jun. 10, 2015

(87) PCT Pub. No.: WO2014/090891
PCT Pub. Date: Jun. 19, 2014

(65) Prior Publication Data
US 2015/0315224 A1 Nov. 5, 2015

(30) Foreign Application Priority Data
Dec. 12, 2012 (EP) .................................... 12196767

(51) Int. Cl.
C07F 15/00 (2006.01)

(52) U.S. Cl.
CPC ........ C07F 15/0066 (2013.01); C07F 15/008 (2013.01); C07F 15/0093 (2013.01)

(58) Field of Classification Search
None
See application file for complete search history.

(56) References Cited

U.S. PATENT DOCUMENTS

| | | | | | |
|---|---|---|---|---|---|
| 4,419,351 | A | * | 12/1983 | Rosenberg | C07F 15/0093 514/184 |
| 4,748,254 | A | * | 5/1988 | Cheltsov-Bebutov | C07F 15/0093 549/206 |
| 5,244,647 | A | * | 9/1993 | Ichiishi | C01G 55/001 423/387 |
| 5,624,919 | A | * | 4/1997 | Farrell | C07F 15/0093 514/184 |
| 5,880,301 | A | * | 3/1999 | Shibasaki | B01J 31/2295 502/162 |
| 7,442,820 | B1 | * | 10/2008 | Voss | C07C 49/92 556/136 |
| 8,273,909 | B2 | * | 9/2012 | Berger | C07F 15/0066 556/137 |
| 2002/0012868 | A1 | * | 1/2002 | Furuse | C23C 18/14 430/270.1 |
| 2006/0106239 | A1 | * | 5/2006 | Kayser | C07F 15/006 556/136 |
| 2010/0234596 | A1 | * | 9/2010 | Watanabe | C07F 15/004 544/225 |
| 2010/0234628 | A1 | * | 9/2010 | Karch | C07C 51/412 556/136 |

FOREIGN PATENT DOCUMENTS

| | | |
|---|---|---|
| DE | 288065 A7 | 3/1991 |
| EP | 512960 A1 | 11/1992 |
| EP | 02116550 A1 | 11/2009 |

OTHER PUBLICATIONS

International Search Report for PCT/EP2013/076263 dated Jan. 28, 2014.
Kukushkin et al., "Influence of the nature of inner-sphere amines on oxidation-reduction potentials of platinum complexes", XP002698524, (1970) Database CA (Online) Chemical Abstracts service.
Felin et al., "Oxidation—Reduction Properties of Platinum Complexes of the Amino Type", Bulletin of the Academy of Sciences of the USR, Division of Chemical Science, Bd. 21, Nr. 4, pp. 880-882 (1972).
Knyazeva et al., "Association of some complexes of platinum(II) and palladium(II) with anions in aqueous solutions", XP002698523 (1979) Database CA (Online) Chemical Abstracts service.
Syamal et al., "Synthesis of new Platinum II) complexes with *ortho*-Phenylenediamine, *ortho*-Aminophenol, Ethanolamine and Oxygen-Donor Ligands", Transition Met. Chem., vol. 8, pp. 280-282 (1983).
Arendse et al., "Synthesis and Characterization of Platinum(II) Complexes of I-Asorbic Acid. Crystal Structure of Ascorbato-C2,O5-ethylenediamineplatinum(II) Dihydrate", Inorg. Chem., vol. 38, pp. 5864-5869 (1999). Inorg. Chem. 1999, 38, 5864-5869.

* cited by examiner

*Primary Examiner* — Joseph D Anthony
(74) *Attorney, Agent, or Firm* — Drinker Biddle & Reath LLP

(57) ABSTRACT

The invention relates to a method for producing aqueous preparations of complexes of platinum group metals (PGM) Pt, Pd, Rh and Ir having the general formula $[M^A/M^B/M^C(L)_a(H_2O)_b(O^{2-})_c(OH^-)_d](OH-)_e(H^+)_f$, wherein $M^A=Pt^{II}$ or $Pd^{II}$, $M^B=Pt^{IV}$, $M^C=Rh$ or Ir, L is a neutral monodentate or bidentate donor ligand, and a is an integer between 1 and 4 (or 2) and/or between 1 and 6 (or 3), b is an integer between 0 and 3 (or 5), c is an integer between 0 and 3 (or 4), d is an integer between 0 and 3 (or 5), e is an integer between 0 and 2 (or 3 or 4) and f is an integer between 0 and 4 (or 5). In the method according to the invention, the hydroxo complexes $H_2Pd(OH)_4$ (in the case of $M^A=Pd^{II}$), $H_2Pt(OH)_6$ (in the case of $M^A=Pt^{II}$ and $M^B=Pt^{IV}$) or $H_3M^C(OH)_6$ (for $M^C=Rh^{III}Ir^{III}$) are converted in the presence of the donor ligands, wherein at least one hydroxo group of the hydro complex is exchanged. Preferably, the reaction occurs at temperatures in the range of 40 to 110° C. with a reaction time of between 2 and 24 hours, wherein, where MA=PtII, the conversion additionally occurs in the presence of a reduction agent. The method optionally further comprises an exchange of OH anions bound outside of the complex sphere with other anions (e.g. hydrogen carbonate or carbonate anions). The aqueous preparations contain PGM complexes such as $[Pt(en)_2](OH)_2$, $[Pt(EA)_4](OH)_2$ or $[Rh(NH_3)_6](OH)_3$ and are used to produce electroplating baths, heterogeneous catalysts or metal powders, for example.

24 Claims, No Drawings

METHOD FOR PRODUCING AQUEOUS PREPARATIONS OF COMPLEXES OF PLATINUM GROUP METALS

CROSS-REFERENCE TO RELATED APPLICATIONS

This application is a national stage application (under 35 U.S.C. §371) of PCT/EP2013/076263, filed Dec. 11, 2013, which claims benefit of European Application No. 12196767.3, filed Dec. 12, 2012, both of which are incorporated herein by reference in their entirety The present invention relates to a process for preparing water-containing compounds and complexes of the platinum group metals and also preparations, solutions and downstream products thereof. The water-containing preparations of the platinum group metal complexes produced by the process are low in halogens and are used, for example, as noble metal components in electroplating baths and also as precursors for producing heterogeneous catalysts, for example automobile exhaust gas catalysts or supported catalysts.

For the purposes of the present patent application, platinum group metals (hereinafter referred to as "PGM" for short) are the metals of the second and third series of transition group 8 of the Periodic Table of the Elements (PTE), i.e. the metals ruthenium (Ru), rhodium (Rh), palladium (Pd), osmium (Os), iridium (Ir) and platinum (Pt). The invention preferably relates to the compounds of the platinum group metals platinum (Pt), palladium (Pd), rhodium (Rh) and iridium (Ir). For the purposes of the present patent application, "PGM-ammine complexes" are complexes of the platinum group metals with ammonia ligands ($NH_3$ ligands). Such complexes are sometimes also referred to as "ammoniates". Examples are hexaamminerhodium(III) trichloride $[Rh(NH_3)_6]Cl_3$ or tetraammineplatinum(II) dichloride $[Pt(NH_3)_4]Cl_2$.

The designation "PGM-amine complexes" is used collectively for complexes of the platinum group metals with amino, alkylamino, dialkylamino, hydroxyalkylamino and alkoxyamino ligands. The term preferably refers to the ligands ethylenediamine (abbreviated to "en" in the present patent application) and 2-aminoethanol (ethanolamine, abbreviated to "EA" in the present patent application).

Many of the simple and commercially available PGM compounds, for example palladium chloride ($PdCl_2$), hexachloroplatinic acid ($H_2PtCl_6$), or ammine compounds of the platinum group metals, e.g. $Pt(NH_3)_4Cl_2$, contain halides, in particular chloride ions. Chloridic solutions or solids of the PGMs typically represent the industrial starting materials for the preparation of the corresponding higher-value compounds. These chloride-containing solutions or solids are obtained by dissolution of the pure noble metals or else as products of noble metal recycling processes. The PGM-containing products (for example supported catalysts or electroplating baths) produced using these compounds are contaminated with chloride residues, which is undesirable for, inter alia, corrosion reasons. Thus, for example, chloride-containing noble metal baths in electroplating technology attack the plant material. Catalysts which are produced using chloride-containing precursors can likewise have a corrosive action and display reduced activity and also a shortened life.

In addition, it is known that chlorine-containing PGM salts, in particular chlorine-containing Pt salts, are hazardous to health and can, for example, trigger allergies; they are therefore undesirable for reasons of occupational hygiene.

In the following, the designation "low-halide" or "low-chloride" or "low-chlorine" refers to a total halogen value or total chlorine content of <5000 ppm, preferably <2000 ppm (measurement by, for example, the Wickbold method, based on the respective metal content of the preparation). The halogens encompass the group fluorine, chlorine, bromine and iodine, and the term halides is used to refer to the corresponding anions $F^-$, $Cl^-$, $Br^-$ and $I^-$.

For the abovementioned reasons, the search for suitable, commercially attractive low-halogen compounds or preparations of the platinum group metals is an important field of work in industrial noble metal chemistry. Even though many low-halogen compounds, for example the nitrates or sulfates of the platinum group metals, e.g. platinum nitrate, rhodium nitrate, palladium sulfate, and also more complex substances such as $[(NH_3)_4Pd](HCO_3)_2$ are commercially available, the search for new substances is a field of work being continuously pursued.

PRIOR ART

Many of the PGM compounds which are halogen-free according to their formula still have high residual halogen contents which result from the production process thereof and can be reduced only by complicated and thus expensive processes, e.g. ion exchange processes. Various halogen-free PGM compounds can be prepared only by means of such ion exchange processes. This applies particularly to compounds of platinum and rhodium; in the case of palladium, the chlorine-free compounds palladium nitrate and palladium sulfate are directly accessible as aqueous solutions.

Thus, EP 512,960 A1 and U.S. Pat. No. 5,244,647 disclose a process for preparing low-chlorine hexaamminerhodium(III) trihydroxide $[Rh(NH_3)_6](OH)_3$ and tetraammineplatinum(II) dihydroxide $[Pt(NH_3)_4](OH)_2$, which uses a process involving ion exchangers for removing the chloride ions. Here, the compounds $[Rh(NH_3)_6]Cl_3$ or $[Pt(NH_3)_4]Cl_2$ are used as starting materials. The compound $[Rh(en)_3](OH)_3$ is also known and has the CAS No. 198292-46-5. However, the preparation of this compound is not described.

DD 288065 describes a process for preparing pure tetraamminepalladium(II) dihydrogencarbonate $[Pd(NH_3)_4](HCO_3)_2$, in which a $[Pd(NH_3)_4]X_2$ complex ($X=Cl^-$, $NO_3^-$) is reacted with a cation exchanger and an ammonium hydrogencarbonate solution.

Further examples for low-chlorine (or low-chloride) PGM compounds are tetraammineplatinum(II) dihydrogencarbonate $[Pt(NH_3)_4](HCO_3)_2$, tetraammineplatinum(II) diacetate $[Pt(NH_3)_4](CH_3COO)_2$, tetraammineplatinum(II) dinitrate $[Pt(NH_3)_4](NO_3)_2$ or tetraamminepalladium(II) diacetate $[Pd(NH_3)_4](CH_3COO)_2$. Here, the chlorine-free salt solutions are each case obtained from the corresponding hydrogen carbonates (solids) in multistage processes.

EP 2,116,550 B1 describes a method of preparing chlorine-free complexes of palladium(II) hydrogencarbonate with amine ligands, in which tetraamminepalladium(II) dihydrogencarbonate $[Pd(NH_3)_4](HCO_3)_2$ is reacted with an organic amine ligand with removal of the ammonia. The process has a number of stages and is very time-consuming since it takes a relatively long time for the ammonia to have been completely driven off.

A. Syamal and B. K. Gupta (Transition Met. Chem. 8, 280-282, 1983) describe the preparation of square planar platinum(III) complexes with N-containing chelating ligands and oxygen-containing ligands (e.g. oxalate or acetate). The latter are datively bound directly to the central Pt(II) atom, i.e. they are within the coordination sphere of the central Pt(II) atom. The preparation of such complexes (for example Pt(II)(NH$_2$C$_2$H$_4$OH)(CH$_3$COO)$_2$) starts out from chlorine-containing compounds such as K$_2$PtCl$_4$. The complexes described by Syamal and Gupta differ in terms of their structure from the Pt(II) complexes of the present invention; since chlorine-containing compounds are also used as starting materials in the preparation, complicated methods of removing the chloride ions are also necessary here.

Conventional halogen-free PGM compounds, for example the nitrates or sulfates of the platinum group metals, have sulfur or nitrogen atoms which in a pyrolysis reaction liberate environmentally polluting sulfur oxides or nitrogen oxides. For this reason, preference is given to PGM precursor compounds which on heating undergo a residue-free decomposition and do not have any N atoms or S atoms. In summary, the low-halogen PGM compounds mentioned are generally expensive because of their multistage preparative processes and the complicated purification steps (e.g. ion exchange processes) and are not very feasible as starting materials for industrial processes.

It is therefore an object of the present invention to provide an economical and inexpensive process for preparing low-halogen, in particular low-chlorine, PGM compounds and water-containing preparations and solutions thereof. These preparations or solutions should have a pH in the range from weakly acidic to basic. Furthermore, preparations which contain hitherto unknown PGM complexes should be made available.

This object is achieved by provision of the process as claimed in the accompanying claims. Furthermore, novel PGM-containing preparations which can be obtained by means of process of the invention are provided.

SUMMARY OF THE INVENTION

The invention relates to a process for producing water-containing preparations of compounds and complexes of the platinum group metals (PGM), in particular the metals platinum (Pt), palladium (Pd), rhodium (Rh) and iridium (Ir). The invention encompasses essentially three embodiments.

In a first embodiment, the invention provides a process for producing water-containing preparations of complexes of the platinum group metals (PGM) having the general formula (1)

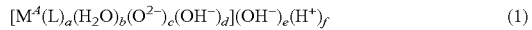 (1)

where
  $M^A$=platinum (Pt) or palladium (Pd) in the oxidation state +2 and
  L=an uncharged monodentate or bidentate donor ligand and
  a=an integer from 1 to 4 (for monodentate donor ligands) or an integer from 1 to 2 (for bidentate donor ligands),
  b=an integer from 0 to 3,
  c=an integer from 0 to 3,
  d=an integer from 0 to 3,
  e=an integer from 0 to 2 and
  f=an integer from 0 to 4
and the platinum group metal $M^A$ has the coordination number 4,
which process is characterized in that the hydroxo complexes H$_2$Pd$^{II}$(OH)$_4$ (in the case of $M^A$=Pd) or H$_2$Pt$^{IV}$(OH)$_6$ (in the case of $M^A$=Pt) are in each case reacted with an uncharged donor ligand L, where at least one hydroxo group of the hydroxo complex concerned is replaced and in the case of $M^A$=Pt the reaction is carried out in the presence of a reducing agent.

In a further embodiment, the invention provides a process for producing water-containing preparations of complexes of the platinum group metals (PGM) having the general formula (2)

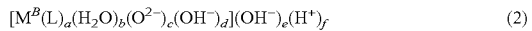 (2)

where
  $M^B$=platinum (Pt) in the oxidation state +4 and
  L=an uncharged monodentate or bidentate donor ligand and
  a=an integer from 1 to 6 (for monodentate donor ligands) or an integer from 1 to 3 (for bidentate donor ligands),
  b=an integer from 0 to 5,
  c=an integer from 0 to 4,
  d=an integer from 0 to 5,
  e=an integer from 0 to 4 and
  f=an integer from 0 to 4
and the platinum group metal $M^B$ has the coordination number 6,
which process is characterized in that the hydroxo complex H$_2$Pt$^{IV}$(OH)$_6$ is reacted with an uncharged donor ligand L, where at least one hydroxo group of the hydroxo complex is replaced. Here, the reaction is carried out without addition of a reducing agent.

In a third embodiment, the invention provides a process for producing water-containing preparations of complexes of the platinum group metals (PGM) having the general formula (3)

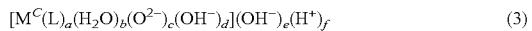 (3)

where
  $M^C$=rhodium (Rh) or iridium (Ir) in the oxidation state +3 and
  L=an uncharged monodentate or bidentate donor ligand and
  a=an integer from 1 to 6 (for monodentate donor ligands) or an integer from 1 to 3 (for bidentate donor ligands),
  b=an integer from 0 to 5,
  c=an integer from 0 to 4,
  d=an integer from 0 to 5,
  e=an integer from 0 to 3 and
  f=an integer from 0 to 5
and the platinum group metal $M^C$ has the coordination number 6,
which process is characterized in that a hydroxo complex of the type H$_3$M$^C$(OH)$_6$ is reacted with an uncharged donor ligand L, where at least one hydroxo group of the hydroxo complex is replaced.

The indices a-f in the general formulae (1), (2) and (3) are selected so that the resulting PGM complexes are electrically neutral.

In all three embodiments of the invention, the reaction is generally carried out at a reaction temperature in the range from 40 to 110° C. and over a reaction time in the range from 2 to 24 hours. Preference is given to a reaction temperature in the range from 45 to 100° C. and a reaction time in the range from 2.5 to 20 hours.

The above-described water-containing PGM-containing preparations are generally aqueous solutions; the reactions are preferably carried out in water as solvent. However, the water-containing preparations can also contain organic, preferably water-miscible, solvents, for example aliphatic alcohols (for example ethanol, isopropanol, butanol, etc.) and/or aliphatic ketones (for example acetone, methyl ethyl ketone, etc.). In these cases, the reaction can also be carried out in such water-containing solvent mixtures.

In the three different embodiments of the process of the invention, the ligand replacement of the OH groups in the hydroxo complexes $H_2Pd(OH)_4$, $H_2Pt^{IV}(OH)_6$ or $H_3M^C(OH)_6$ (in the case of $M^C=Rh^{III}$ or $Ir^{III}$) by the uncharged donor ligands L does not have to be complete, so that mixed complexes can also be present. These can also have aquo ligands (=uncharged $H_2O$ ligands, number b), oxo ligands ($O^{2-}$ ligands, number c) and hydroxo ligands ($OH^-$ ligands, number d) in addition to the uncharged donor ligands L (number a). The electrical neutrality of the resulting PGM complex is achieved by further hydroxo radicals of the type ($OH^-$, number e) which are located outside the complexation sphere. These hydroxo radicals will be referred to as "hydroxy groups" or "hydroxide groups" in the present patent application. In the case of resulting PGM complexes having an overall anionic charge, the presence of protons ($H^+$, number f) has to be taken into account in order to ensure electrical neutrality.

The preparations of the invention contain PGM complexes which in the case of complete hydroxo group replacement are generally cationically charged, and in the case of partial replacement and/or the presence of oxo or hydroxo ligands are also anionically charged or uncharged. The water-containing preparations of the invention are thus in many cases multicomponent mixtures of anionic, cationic or uncharged complexes.

However, in all embodiments of the process of the invention, the replacement of at least one hydroxo group of the respective hydroxo complex by an uncharged donor ligand L occurs, as a result of which, for example, the solubility of the resulting PGM hydroxo complex in water is brought about. The coordination numbers (CN) for monodentate ligands, namely 4 (for $M^A=Pt^{II}$ and $Pd^{II}$, general formula (1)) and 6 (for $M^B=Pt^{IV}$, general formula (2)) and for $M^C=Rh^{III}$ or $Ir^{III}$, general formula (3), are in principle maintained in the complexes of the invention. This applies analogously when bidentate ligands are used.

DETAILED DESCRIPTION OF THE INVENTION

The process of the invention is described in more detail below. The present process in principle starts out from the low-halogen hydroxo complexes of the platinum group elements. In the case of Pt, Pd, Rh and Ir, these are, for example, the starting compounds $H_2Pt(OH)_6$ ("hexahydroxoplatinic(IV) acid"), $H_2Pd(OH)_4$, $H_3Rh(OH)_6$ and $H_3Ir(OH)_6$. These compounds are prepared in various processes known to those skilled in the art by reaction of the respective chlorine-containing starting salts with alkalis such as NaOH, KOH or ammonia in aqueous solution and optionally subsequent neutralization. The best results are obtained when freshly prepared or precipitated hydroxo complexes (cf. examples) are used. In another notation, $H_2Pt(OH)_6$ is written as $Pt(OH)_4 \times 2H_2O$, $H_2Pd(OH)_4$ is written as $Pd(OH)_2 \times 2H_2O$, $H_3Rh(OH)_6$ is written as $Rh(OH)_3 \times 3H_2O$ and $H_3Ir(OH)_6$ is written as $Ir(OH)_3 \times 3H_2O$. Here too, these are generally complex mixtures of substances; however, the different notations are inconsequential to the essence of the present invention.

The hydroxo complexes or hydroxides of the PGMs are generally sparingly soluble in water and can thus easily be separated off and washed by customary methods until they have a low halide content. In the case of $H_2Pt(OH)_6$, residual contents of chlorine of <5000 ppm, preferably <2000 ppm (in each case based on the metal Pt) are achieved. These complexes are thus suitable starting materials for the process of the invention for preparing low-halide PGM compounds. The residual chlorine content of the PGM compounds prepared by the present process can be set via the chlorine content of the hydroxo starting complexes.

It is known to those skilled in the art that in the reaction of the Pt-hydroxo complex $H_2Pt(OH)_6$ with ligands such as ammonia or ethanolamine, the cationic $H^+$ ion is normally replaced and the six-fold OH coordination on the Pt atom is retained. Thus, for example, the reaction of $H_2Pt(OH)_6$ with ammonia or ethanolamine in aqueous solution under mild conditions forms the corresponding ammonium salts of hexahydroxyplatinic acid, cf. eq. (a) and (b):

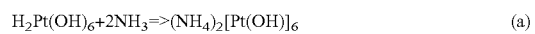

(a)

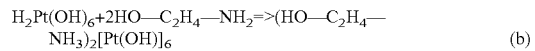

(b)

In these cases, the ligand sphere of the platinum is not changed. The PGM is present in an anionic (i.e. negatively charged) hexacoordinated hydroxo complex.

It has now surprisingly been found that under particular reaction conditions the reaction proceeds differently and the ligand L enters the coordination sphere of the PGM hydroxo compound and direct ligand exchange with the complexed OH ligands thus occurs. This is all the more surprising because the PGM hydroxides have hitherto been considered by those skilled in the art to be insoluble in ammonia (the PGM hydroxides can, inter alia, also be prepared and isolated by precipitation with ammonia).

The reactions according to the invention can be illustrated by way of example by the following equations (where in each case complete ligand exchange is shown).

a) In the case of complexes of the type $[M^A(L)_a(H_2O)_b(O^{2-})_c(OH^-)_d](OH^-)_e(H^+)_f$;
for $M^A=Pd(II)$, a=4, b=0; c=0; d=0; e=2, f=0:

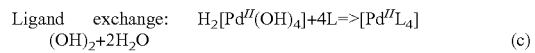

(c)

for $M^A=Pt(II)$, a=4, b=0; c=0; d=0; e=2, f=0:

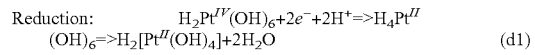

(d1)

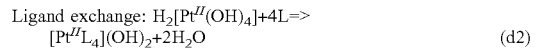

(d2)

Here, L in eq. (c) and (d2) is in each case an uncharged, monodentate donor ligand. When a bidentate ligand L (for example en) is used, a=2. As reducing agents in eq. (d1), preference is given to using the residue-free reducing agents described further below.

b) In the case of complexes of the type $[(M^B(L)_a(H_2O)_b(O^{2-})_c(OH^-)_d](OH^-)_e(H^+)_f$;
for $M^B=Pt(IV)$, a=6, b=0, c=0, d=0, e=4, f=0:

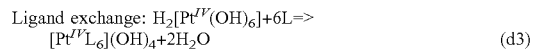

(d3)

c) In the case of complexes of the type $[M^C(L)_a(H_2O)_b(O^{2-})_c(OH^-)_d](OH^-)_e(H^+)_f$;
for $M^C=Rh(III)$ or $Ir(III)$; a=6, b=0, c=0, d=0, e=3, f=0:

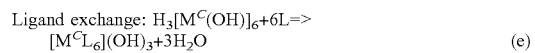

(e)

Here, L in the equations (d3) and (e) is in each case an uncharged monodentate donor ligand; when a bidentate ligand L (for example en) is used, a is accordingly 3.

It should be noted that the abovementioned reaction equations are formal, simplified reaction equations which serve as models and in which complete replacement of the hydroxo groups is shown in each case. However, this is not always the case in practice. As indicated above, partial replacement of the hydroxo ligands is possible, especially since the products are present in aqueous solution. For this reason, not only the abovementioned uncharged donor ligands L but also other donor ligands such as uncharged aquo ligands ($H_2O$) or oxo ligands ($O^{2-}$) or hydroxo ligands can be coordinated to the central PGM. This can, for example in the case of Rh(III), lead to mixes in which further, partially OH-substituted cationic complexes such as $[Rh(NH_3)_5(OH)](OH)_2$ or $[Rh(NH_3)_4(OH)_2](OH)$ (where a=4, b=0, c=0, d=2; e=1, f=0) are present in addition to the main product $[Rh(NH_3)_6](OH)_3$ (a=6, e=3). However, overall uncharged complexes such as $[Rh(NH_3)_3(OH)_3]$ or singly anionic complexes such as $H[Rh(NH_3)_2(OH)_4]^-$ (where a=2, b=0, c=0, d=4; e=0, f=1) can also be formed (cf. example 5).

Furthermore, partially substituted aquo complexes in which the uncharged donor ligands are partly replaced by $H_2O$ molecules can also occur. This can, for example in the case of Pt(IV), lead to mixes in which partially substituted aquo complexes such as $[Pt(NH_3)_5(H_2O)](OH)_4$, $[Pt(NH_3)_4(H_2O)_2](OH)_4$ or $[Pt(NH_3)_3(H_2O)_3](OH)_4$ are present in addition to the main product $[Pt(NH_3)_6](OH)_4$. This also applies analogously to the other platinum group metals of the invention described here.

However, for reasons of clarity and of simplification, complete replacement of the OH ligands in the PGM hydroxo complex concerned by the uncharged donor ligand(s) L is generally assumed for the purposes of the present patent application and the main product formed thereby is indicated in each case.

In the reactions according to the invention, the abovementioned PGM complexes are generally dissolved or dispersed in deionized (DI) water or in a water-containing solvent mixture and the ligand L is added.

The process of the present patent application makes a different coordination chemistry of the platinum group metals possible: in a preferred embodiment, it opens the door to low-halogen platinum(II) or palladium(II) complexes and also to low-halogen rhodium(III) or iridium(III) complexes. In these compounds, the PGM can be present in a cationic (=positively charged), uncharged or weakly anionic (=negatively charged) complex. Should the anion be present as hydroxide anion ($OH^-$) outside the complexation sphere, it can in this case be replaced by other anions in a further step. The process of the invention therefore in principle encompasses ligand exchange (in the case of $M^A$=Pt(II) accompanied by reduction), optionally followed by a further step in which the OH anion bound outside the complexation sphere is replaced by an alternative anion (hereinafter referred to as "anion exchange" for short).

The individual steps of the process of the invention are explained below.

a) Ligand Exchange

In the process of the invention, the ligand exchange (i.e. the reaction with the donor ligand L) is carried out at elevated temperatures and over a prolonged period of time. The temperatures are in the range from 40 to 110° C., preferably in the range from 45 to 100° C. The reaction time is in the range from 2 to 24 hours, preferably in the range from 2.5 to 20 hours. The reaction is preferably carried out in aqueous solution, but, as mentioned above, it is also possible to use organic solvents, e.g. aliphatic alcohols and/or aliphatic ketones, optionally in a mixture with water.

In general, the ligand L is added in the respective stoichiometric ratio to the reaction mixture, but the ligand L can optionally also be added in superstoichiometric amounts. This is, for example, the case for ammonia ($NH_3$) in order to compensate for vaporization losses over prolonged reaction times.

Suitable ligands L are monodentate or bidentate, uncharged donor ligands which make available 2 electrons (in the case of monodentate ligands) or 4 electrons (in the case of bidentate ligands) in each case.

As monodentate donor ligands, use is generally made of ligands from the group consisting of monoalkylamines, dialkylamines, trialkylamines, monoalkanolamines, dialkanolamines, trialkanolamines, monoarylamines, diarylamines, triarylamines, trialkylphosphines, triarylphosphines, trialkoxyphosphines, triaryloxyphosphines (triaryl phosphites) and mixtures thereof and ammonia. Examples of preferred monodentate ligands are the nitrogen-containing ligands ammonia ($NH_3$), ethylamine, diethylamine, ethanolamine ("EA") or isopropanolamine. Examples of suitable P-containing monodentate donor ligands are triphenylphosphine, tricyclohexylphosphine and phosphites such as triphenyl phosphite.

As bidentate donor ligands, use is made in each case of ligands from the group consisting of alkylenediamines, arylenediamines, alkylenediphosphines or arylenediphosphines and mixtures thereof. Examples of preferred bidentate ligands are ethylenediamine ("en"), o-phenylenediamine, trimethylenediamine, tetramethylenediamine, pentamethylenediamine, hexamethylenediamine or 1,2-propylenediamine. An example of a suitable bidentate P-containing ligand is 1,2-bis(diphenylphosphino)ethane.

Tridentate or polydentate donor ligands can also be used analogously. Examples of tridentate ligands are diethylenetriamine ($H_2N-CH_2-CH_2-NH-CH_2-CH_2-NH_2$, DETA) or dipropylenetriamine. Examples of polydentate ligands are trimethylenetetramine or hexamethylenetetramine. The numerical values of the parameter a should be adapted appropriately. Mixtures of the abovementioned ligands are also possible.

Particular preference is given to using nitrogen-containing monodentate or bidentate donor ligands. Very particular preference is given to using the ligands ammonia ($NH_3$), ethanolamine ("EA"), ethylenediamine ("en") or mixtures thereof. Examples of water-containing preparations according to the invention prepared by ligand exchange are preparations which contain complexes having the following composition as main product:

for $M^A$=Pd(II): $[Pd(NH_3)_4](OH)_2$, $[Pd(en)_2](OH)_2$
for $M^B$=Pt(IV): $[Pt(EA)_6](OH)_4$
for $M^C$=Rh(III), Ir(III): $[Rh(NH_3)_6](OH)_3$, $[Rh(en)_3](OH)_3$, $[Ir(en)_3](OH)_3$.

b) Reduction

A specific case is the preparation of low-halide Pt(II) compounds. According to the invention, the Pt-hydroxo complex in the oxidation state +IV (i.e. $H_2Pt^{IV}(OH)_6$) is used as starting material and is reacted with the ligand L in the presence of a reducing agent, with the tetravalent Pt(IV) being reduced to divalent Pt(II). The reducing agents suitable for this purpose are known to those skilled in the art; preference is given to using "residue-free" reducing agents, i.e. ones which after the reduction reaction leave behind no residues or only small residues in the product solution and generally do not have to be separated off. Examples of such "residue-free" reducing agents are hydrogen ($H_2$) and hydrogen-comprising mixtures such as $N_2/H_2$ 80/20 or 95/5; also hydrazine ($N_2H_4$), formaldehyde (HCHO), oxalic acid ($H_2C_2O_4$) or formic acid (HCOOH). To reduce Pt(IV) to Pt(II), the reducing agent is added in the redox equivalent ratio of from 1:1 to 2:1 (based on Pt). Preference is given to using equivalent amounts of reducing agent, and the addition is generally carried out simultaneously with the addition of the ligand(s) in aqueous solution.

Examples of such preparations according to the invention prepared by ligand exchange and simultaneous reduction are preparations which contain Pt(II) complexes having the following composition as main product:

[Pt(en)$_2$](OH)$_2$, [Pt(NH$_3$)$_4$](OH)$_2$, [Pt(EA)$_4$](OH)$_2$ c) Anion Exchange The process of the invention can also comprise replacement of the hydroxy anions of the type (OH$^-$)$_e$ in the complexes of the general formulae

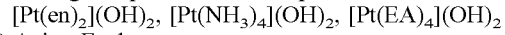

$$[M^A(L)_a(H_2O)_b(O^{2-})_c(OH^-)_d](OH^-)_e(H^+)_f \quad (1)$$

$$[M^B(L)_a(H_2O)_b(O^{2-})_c(OH^-)_d](OH^-)_e(H^+)_f \quad (2)$$

$$[M^C(L)_a(H_2O)_b(O^{2-})_c(OH^-)_d](OH^-)_e(H^+)_f \quad (3)$$

by one or more anions of inorganic or organic acids. In the indicated formulae (1), (2) and (3), the meanings of $M^A$, $M^B$, $M^C$, L, a, b, c, d, e and f are as defined above in the previous sections. In this anion exchange, a neutralization, i.e. a replacement of the hydroxy anions (OH$^-$)$_e$ by the appropriate acid anions, takes place in principle, and water is formed. To carry out the anion exchange, cationic complexes in which index e≠0 should be present. e is preferably an integer from 1 to 4, particularly preferably 2, 3 or 4, and f is preferably 0.

Suitable acids are, for example, acetic acid (CH$_3$COOH), formic acid, oxalic acid (H$_2$C$_2$O$_4$) or carbonic acid (or carbonates and hydrogencarbonates), or else sulfuric acid, phosphoric acid, tetrafluoroboric acid (HBF$_4$) or nitric acid. As anions of inorganic or organic acids, it is possible to use anions from the group consisting of acetates, formates, oxalates, carbonates, hydrogencarbonates, sulfates, nitrates, phosphates, tetrafluoroborates and mixtures thereof.

It is advantageous to react equimolar amounts of these acids with the basic PGM-hydroxy complexes in an aqueous or water-containing solution or preparation. The reaction temperatures are generally in the range from 25 to 100° C., and suitable reaction times are in the range from 30 minutes to 3 hours. This gives low-halogen, acidic to neutral PGM compounds which are generally present in an aqueous solution or preparation and are processed further in this form.

In the case of the hydroxy compounds of the type [M$^A$(L)$_a$](OH)$_2$ (M$^A$=Pt$^{II}$, Pd$^{II}$, b=c=d=f=0, e=2) as an example, this anion exchange can be represented schematically by the equation (f):

$$[M^A(L)_a](OH)_2 + 2H^+X^- \Rightarrow [M^A(L)_a]^{2+}X_2 + 2H_2O \quad (f)$$

Here, X$^-$ is a singly negatively charged acid anion, for example HCO$_3^-$, CH$_3$COO$^-$, HCOO$^-$ or NO$_3^-$. In the case of doubly negatively charged anions Y$^{2-}$ (for example CO$_3^{2-}$, C$_2$O$_4^{2-}$, SO$_4^{2-}$), the anion exchange can be represented according to equation (g):

$$[M^A(L)_a](OH)_2 + (H^+)_2Y^{2-} \Rightarrow [M^A(L)_a]^{2+}Y + 2H_2O \quad (g)$$

In the case of the PGM-hydroxy compounds of the type [M$^B$(L)$_a$]$^{4+}$(OH)$_4$ (M$^B$=Pt$^{IV}$, b=c=d=f=0, e=4) and [M$^C$(L)$_a$]$^{3+}$(OH)$_3$ (M$^C$=Rh, Ir, b=c=d=f=0, e=3), too, and also correspondingly for triply negatively charged anions such as PO$_4^{3-}$, the anion exchange proceeds analogously.

Examples of such water-containing preparations according to the invention produced via anion exchange are preparations which contain complexes having the following composition as main product:

for M$^A$=Pd(II): [Pd(NH$_3$)$_4$](HCO$_3$)$_2$, [Pd(en)$_2$](CH$_3$COO)$_2$, [Pd(NH$_3$)$_4$]SO$_4$ for M$^B$=Pt(II): [Pt(en)$_2$](CO$_3$), [Pt(EA)$_4$](C$_2$O$_4$), [Pt(EA)$_4$](CH$_3$COO)$_2$

[Pt(NH$_3$)$_4$](HCO$_3$)$_2$, [Pt(EA)$_4$]CO$_3$, [Pt(EA)$_4$](HCO$_3$)$_2$ for M$^B$=Rh(III) [Rh(NH$_3$)$_6$](CH$_3$COO)$_3$ for M$^B$=Ir(III) [Ir(NH$_3$)$_6$](PO$_4$)$_3$ Characterization of the Complexes The compounds and complexes of the present invention are in most cases mixtures in which variously coordinated PGM complexes are present side-by-side in a water-containing or aqueous preparation or solution. The concentration of the respective PGM (Pt, Pd, Rh or Ir) is in the range from 0.5 to 15% by weight (based on the total weight of the preparation or solution).

The low-halogen water-containing or aqueous preparations, mixtures or solutions according to the invention generally have a weakly acidic to basic pH. Thus, the pH of the water-containing preparations of the invention is in the range pH 5 to 14, preferably in the range pH 7 to 14 and particularly preferably in the range pH 7 to 12.

The characterization of the preparations or solutions and complexes is carried out by conventional analytical methods such as capillary electrophoresis; the determination of the Pt, Pd, Rh or Ir content can be carried out by means of ICP ("inductively coupled plasma") or by gravimetric methods.

$^{195}$Pt-NMR Spectroscopy

The coordination sphere of the PGM complexes of the invention can in the case of platinum be determined by means of $^{195}$Pt-NMR spectroscopy. The measurements are carried out using a BRUKER AVANCE 400 (from Bruker BioSpin GmbH, Rheinstetten, DE); H$_2$PtCl$_6$ in D$_2$O is used as external reference (δ=0 ppm), and a DMSO capillary is used as "locking solvent". The chemical shifts of the Pt(II) complexes of the invention are in the range from δ=−2000 to −3200 ppm. In the [Pt(NH$_3$)$_4$](OH)$_2$ solution prepared according to the invention, it is possible to confirm, for example, the existence of the square planar [Pt(NH$_3$)$_4$]$^{2+}$ cation by means of the signal at δ=−2576 ppm.

Determination of the Chlorine Content

The chlorine content of the PGM-containing preparations of the invention is typically in the range <5000 ppm, preferably <2000 ppm (total chlorine content, based on the respective PGM content). The determination of the chlorine content is carried out by a method which comprises the steps: (1) taking-up of the sample in a suitable solvent, (2) combustion in an H$_2$/O$_2$ flame, (3) collection of the condensate in sodium hydroxide solution and (4) determination of the chlorine content by ion chromatography (IC). This method is known as "total chlorine analysis by the Wickbold method". However, other, equivalent methods can also be used.

The water-containing, PGM-containing preparations or solutions are employed in many fields of use. They can be used as PGM precursors, for example in electroplating baths or for producing homogeneous or heterogeneous catalysts. Furthermore, they can be used for producing high-purity PGM-containing powders and for the preparation of further complexes. For the purposes of the present invention, the expression "further complexes" refers to complexes which are different from the complexes used in the respective reaction. This can be brought about, for example, by reduction, oxidation, ligand exchange on the complexes used or combinations thereof. Oxidations and reductions of the complexes used also encompasses reactions in which only the respective metal atom or only one or more ligands change their oxidation number or oxidation state. The water-containing preparations obtained by the process of the present patent application can thus undergo a reaction to obtain further products, for example electroplating baths, homogeneous or heterogeneous catalysts, metal powders or further complexes. In addition to or instead of a reaction, formulation of the water-containing preparations obtained by the process of the present patent application can also take place, including, inter alia, addition of further constituents, for example of auxiliaries or solvents, replacement of constituents, for example the solvent, and/or the removal of constituents, e.g. the removal of by-products or unreacted starting materials, but also solvents. The removal of solvents can also be carried out in order to formulate the preparation so as to increase, for example, the concentration of the other constituents.

The following examples illustrate the invention in more detail but without restricting the scope of protection thereof.

General Preliminary Remarks

The reactions described below are carried out under an air atmosphere using deionized water (DI water) as solvent. In general, glass flasks provided with reflux condenser and dropping funnel are used.

The PGM hydroxo complexes $H_2Pt(OH)_6$ or $Pt(OH)_4 \times 2H_2O$ ("hexahydroxoplatinic(IV) acid"), $H_2Pd(OH)_4$ or $Pd(OH)_2 \times 2H_2O$, $H_3Rh(OH)_6$ or $Rh(OH)_3 \times 3H_2O$ and $H_3Ir(OH)_6$ or $Ir(OH)_3 \times 3H_2O$ are generally freshly prepared before the respective reaction. For this purpose, the hydroxides are precipitated from chloridic solution by means of alkali metal/alkaline earth metal hydroxide or ammonia, separated off and washed to a low halide content with DI water. The appropriate methods and sequences of operations are known to a person skilled in the field of noble metal chemistry.

Example 1

(Tetraammine)Platinum(II) Hydroxide Solution 5 g of Pt (25.6 mmol) as $H_2Pt(OH)_6$ (freshly precipitated, manufacturer Umicore AG & Co KG, Hanau) are placed together with 150 g of 25% strength ammonia solution and 100 ml of DI water in a glass flask provided with reflux condenser and heated. At a temperature of 40° C., 1.19 g of formic acid (25.6 mmol) diluted in 50 ml of water are added. The reaction mixture is heated (T=70-80° C.) overnight (about 16 hours). A clear, colorless solution containing small amounts of fully reduced platinum as grey solid is formed. Analysis of the clear supernatant solution indicates a content of 1.58% by weight of Pt; this corresponds to a yield of 92% (based on the Pt used). The $[Pt^{II}(NH_3)_4]^{2+}$ cation is identified in the solution prepared by means of capillary electrophoresis (signal at a retention time of from 2 to 2.5 minutes).

Furthermore, the existence of the $[Pt(NH_3)_4]^{2+}$ cation is confirmed by means of $^{195}$Pt-NMR spectroscopy (chemical shift at δ=−2576 ppm). The total chlorine content of the aqueous (tetraammine)platinum(II) hydroxide solution is 560 ppm based on platinum (Wickbold method).

Example 2

Bis(Ethylenediamine)Platinum(II) Hydroxide Solution 5 g (25.6 mmol) of Pt as $H_2Pt(OH)_6$ (manufacturer Umicore AG & Co KG, Hanau) are placed together with 3.08 ml (51.2 mmol) of ethylenediamine (for synthesis, Merck) and 100 ml of DI water in a glass flask provided with reflux condenser and heated while stirring. At 60° C., 1.19 g of formic acid (25.6 mmol) diluted in 50 ml of water are added via a dropping funnel. The reaction mixture is heated at 75° C. overnight (about 15 hours). A yellow-orange solution is formed. The Pt content of the solution is 0.58% by weight, corresponding to a yield of 32% of the platinum used.

Example 3

(Tetraammine)Palladium(II) Hydroxide Solution 10.0 g (0.094 mol) of palladium in the form of 41 g of freshly precipitated moist palladium hydroxide ($Pd(OH)_2 \times 2H_2O$; manufacturer Umicore AG & Co KG, Hanau) which has been washed free of chloride are introduced into a tiered 250 ml three-necked flask and made up with DI water to a total amount of 50 g. 35.5 ml of 25% strength ammonia solution are added while stirring. The solution is subsequently heated to 65° C. under reflux while stirring and maintained at this temperature for 2.5 hours. The solution formed is cooled to room temperature (about 23° C.), admixed with 0.2 g of activated carbon (Norit SC) and stirred at room temperature for one hour. The mixture is filtered through a blue band filter and washed with 10 ml of DI water. This gives 87.2 g of a yellow-orange solution. The solution contains 11.13% by weight of Pd. This corresponds to a yield of 97.05% based on palladium used. The total chlorine content of the solution is 809 ppm (based on Pd).

Capillary electrophoresis proves the presence of the $[Pd(NH_3)_4]^{2+}$ cation by cross-comparison with $Pd(NH_3)_4$ compounds which were prepared by a conventional method (i.e. main signal at a retention time of 2.5 minutes).

Example 4

Bis(Ethylenediamine)Palladium(II) Hydroxide Solution 10.0 g (0.093 mol) of palladium in the form of about 37 g of freshly precipitated moist palladium hydroxide ($Pd(OH)_2 \times 2H_2O$; manufacturer Umicore AG & Co KG, Hanau) which has been washed free of chloride are placed in a tiered three-neck flask and made up with DI water to a total mass of 70 g. The three-necked flask is provided with a reflux condenser, the reaction mixture is stirred by means of a magnetic stirrer and the temperature is controlled by means of an oil bath. The oil bath temperature is about 23° C. 11.2 g of ethylenediamine (0.186 mol; for synthesis, Merck) are mixed with 12.4 g of DI water in a glass beaker and cooled to a temperature of about 18-20° C. (water/ice bath).

The aqueous ethylenediamine solution is added all at once to the stirred palladium hydroxide suspension. The reaction mixture is heated for 18 hours by setting of an oil bath temperature of 45° C. while stirring. The resulting yellow-orange, largely clear solution is cooled to room temperature (about 23° C.). 0.5 g of activated carbon (Norit SC, Norit Deutschland GmbH) is subsequently added and the mixture is stirred at room temperature for 1 hour. The solid is subsequently filtered off on a blue band filter. The reaction flask is rinsed with 10 ml of DI water and this water is filtered through the blue band filter with activated carbon and added to the product solution. This gives 98.7 g of a clear yellow solution. The solution contains 9.94% by weight of Pd. This corresponds to a yield of 98.1% based on palladium used. The total chlorine content of the solution is 804 ppm based on palladium.

Example 5

(Hexaammine)Rhodium(III) Hydroxide Solution 9.92 g of rhodium (0.0964 mol) in the form of about 31.4 g of moist, freshly precipitated rhodium hydroxide ($H_3Rh(OH)_6$ or $Rh(OH)_3 \times 3H_2O$, manufacturer Umicore AG & Co KG, Hanau) which has been washed to a low halide content are admixed in a 250 ml three-neck flask with DI water so that the total weight of the suspension in the flask is 75 g. The flask is provided with a magnetic stirrer and reflux condenser and 44 ml of 25% strength ammonia solution (corresponding to 11 g of $NH_3$=0.65 mol) is added all at once at room temperature while stirring. The mixture is heated while stirring to an internal temperature of 75° C. and the solution is heated at this temperature for 20 hours. The reaction mixture is subsequently cooled to room temperature (about 23° C.) by means of a water/ice bath and admixed with 0.5 g of activated carbon (Norit SC). The mixture is stirred at room temperature for 1 hour and subsequently filtered through a blue band filter. The reaction flask is rinsed with 10 ml of DI water and this is added via the filter to the reaction mixture. 116.1 g of a clear orange solution result. The solution contains 8.34% by weight of Rh. This corresponds to a yield of 97.6% based on rhodium used. The total chlorine content of the solution is 1210 ppm (based on Rh).

Capillary electrophoresis shows three signals; a signal (1) in the weakly anionic region, a small signal (2) at the neutral point and a medium strength signal (3) in the cationic region. This indicates a product mixture in which some hydroxo ligands have been replaced by $NH_3$, but not completely. Apart from the target compound $[Rh(NH_3)_6](OH)_3$ (signal (3)), the uncharged partially substituted complex $[Rh(NH_3)_3(OH)_3]$ (signal (2)) can be present. The signal position of the anionic complex (1) indicates only a small negative charge and can be assigned to the complex $H[Rh(NH_3)_2(OH)_4]$.

Example 6

Tris(Ethylenediamine)Rhodium(III) Hydroxide Solution 200 g of rhodium (1.94 mol) in the form of 711.7 g of moist, freshly precipitated rhodium hydroxide ($H_3Rh(OH)_6$ or $Rh(OH)_3 \times 3H_2O$, manufacturer Umicore AG & Co KG, Hanau) which has been washed to a low halide content are admixed in a tiered 2 l three-neck flask with DI water so that the total weight of the suspension in the flask is 1000 g. The flask is provided with a precision glass stirrer and reflux condenser and 350.5 g (5.82 mol) of ethylenediamine (for synthesis, Merck) are added all at once while stirring at room temperature. The reaction mixture is heated while stirring by application of an oil bath temperature of 60° C. The oil bath temperature is slowly increased to 90° C. over a period of 3 hours. From about 74° C., a slightly exothermic reaction is observed and the solid begins to dissolve. After 3 hours, the reaction mixture is cooled to room temperature (about 23° C.) by means of a water/ice bath and admixed with 5 g of activated carbon (Norit SC). The reaction mixture is stirred at room temperature for 1 hour and subsequently filtered through a blue band filter. The reaction flask is rinsed with 100 ml of DI water and this is added via the filter to the reaction mixture. 1814.4 g of a clear orange solution result. The solution contains 11.0% by weight of Rh. An Rh-based isolated yield of 99.8% is thus obtained. The total chlorine content of the solution is 910 ppm (based on rhodium).

Capillary electrophoresis shows two cationic signals which can be assigned to the compounds $[Rh(en)_3](OH)_3$ (main signal) and $[Rh(en)_2(OH)_2]OH$ (weak signal).

Example 7

Tris(Ethylenediamine)Rhodium(III) Acetate Solution 5.06 g of rhodium (49.2 mmol) in the form of 50.0 g of (trisethylenediamine)rhodium(III) hydroxide solution (about 10% by weight of Rh, prepared as described in example 6) are weighed into a 100 ml three-neck flask. While stirring, 10.58 ml of 100% strength acetic acid are slowly added dropwise at room temperature (about 23° C.) until a pH of 7 has been reached. The dropwise addition time is about 30 minutes; gentle evolution of heat occurs. The Rh content of the clear yellow solution obtained is 8.2% by weight.

The invention claimed is:

1. A process for producing water-containing preparations of complexes of the platinum group metals (PGM) having the general formula (1), (2) or (3)

where $M^A$=platinum (Pt) or palladium (Pd) in the oxidation state +2 and

L=an uncharged monodentate or bidentate donor ligand and a=an integer from 1 to 4 (for monodentate donor ligands) or an integer from 1 to 2 (for bidentate donor ligands), b=an integer from 0 to 3, c=an integer from 0 to 3, d=an integer from 0 to 3, e=an integer from 0 to 2 and f=an integer from 0 to 4 and the platinum group metal $M^A$ has the coordination number 4, wherein the hydroxo complexes $H_2Pd(OH)_4$ (in the case of $M^A$=Pd) or $H_2Pt(OH)_6$ (in the case of $M^A$=Pt) are in each case reacted with an uncharged donor ligand L, where at least one hydroxo group of the hydroxo complex concerned is replaced and in the case of $M^A$=Pt the reaction is carried out in the presence of a reducing agent or

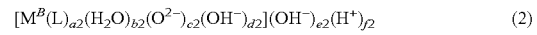

where $M^B$=platinum (Pt) in the oxidation state +4 and

L=an uncharged monodentate or bidentate donor ligand and a2=an integer from 1 to 6 (for monodentate donor ligands) or an integer from 1 to 3 (for bidentate donor ligands), b2=an integer from 0 to 5, c2=an integer from 0 to 4, d2=an integer from 0 to 5, e2=an integer from 0 to 4 and f2=an integer from 0 to 4 and the platinum group metal $M^B$ has the coordination number 6, wherein the hydroxo complex H₂Pt(OH)₆ is reacted with an uncharged donor ligand L, where at least one hydroxo group of the hydroxo complex is replaced
or

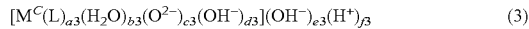    (3)

where
$M^C$=rhodium (Rh) or iridium (Ir) in the oxidation state +3 and
L=an uncharged monodentate or bidentate donor ligand and
a3=an integer from 1 to 6 (for monodentate donor ligands) or an integer from 1 to 3 (for bidentate donor ligands),
b3=an integer from 0 to 5,
c3=an integer from 0 to 4,
d3=an integer from 0 to 5,
e3=an integer from 0 to 3 and
f3=an integer from 0 to 5
and the platinum group metal $M^C$ has the coordination number 6,
wherein a hydroxo complex of the type $H_3M^C(OH)_6$ is reacted with an uncharged donor ligand L, where at least one hydroxo group of the hydroxo complex is replaced and
wherein the water-containing preparations have a pH in the range of 5 to 14.

2. The process as claimed in claim 1, wherein the PGM has the general formula (1).

3. The process as claimed in claim 1, wherein the PGM has the general formula (2).

4. The process as claimed in claim 1, wherein the PGM has the general formula (3).

5. The process as claimed in claim 1, wherein the indices a-f in the general formulae (1), a2-af2 in formula (2) or a3-f3 in formula (3) are selected so that the resulting PGM complexes are electrically neutral.

6. The process as claimed in claim 1, wherein the reaction temperature is in the range from 40 to 110° C.

7. The process as claimed in claim 1, wherein the reaction time is in the range from 2 to 24 hours.

8. The process as claimed in claim 1, wherein said monodentate donor ligands are ammonia or ligands selected from the group consisting of monoalkylamines, dialkylamines, trialkylamines, monoalkanolamines, dialkanolamines, trialkanolamines, monoarylamines, diarylamines, triarylamines, trialkylphosphines, triarylphosphines, trialkoxyphosphines, triaryloxyphosphines and mixtures thereof.

9. The process as claimed in claim 7, wherein said monodentate donor ligands are ammonia, ethanolamine, ethylamine, diethylamine, isopropanolamine or mixtures thereof.

10. The process as claimed in claim 1, wherein said bidentate donor ligands are alkylenediamines, arylenediamines, alkylenediphosphines, arylenediphosphines or mixtures thereof.

11. The process as claimed in claim 10, wherein said bidentate donor ligands are ethylenediamine, o-phenylenediamine, trimethylenediamine, tetramethylenediamine, pentamethylenediamine, hexamethylenediamine, 1,2-propylenediamine or mixtures thereof.

12. The process as claimed in claim 1, wherein the replacement of the OH groups in the hydroxo complexes H₂Pd(OH)₄, H₂Pt(OH)₆ or $H_3M^C(OH)_6$ (in the case of $M^C$=Rh$^{III}$ or Ir$^{III}$) by the uncharged donor ligands L is incomplete and the resulting compounds of the general formulae (1), (2) or (3) continue to contain aquo (H₂O), oxo (O²⁻) or hydroxo (OH⁻) ligands.

13. The process as claimed in claim 1, wherein hydrogen, an H₂/N₂ mixture, hydrazine (N₂H₄), oxalic acid (H₂C₂O₄), formaldehyde (HCHO) or formic acid (HCOOH) or mixtures thereof are used as reducing agent in the case of $M^A$=platinum(II).

14. The process as claimed in claim 1, wherein the water-containing preparations are aqueous solutions and the reaction is carried out in aqueous solution.

15. The process as claimed in claim 1, wherein the water-containing preparations contain organic solvents and the reaction is carried out in water-containing solvent mixtures.

16. The process as claimed in claim 1, wherein the concentration of the platinum group metals $M^A$, $M^B$ or $M^C$ in the water-containing preparation is in the range from 0.5 to 15% by weight.

17. The process as claimed in claim 1, wherein the total halogen content, in particular the total chlorine content, of the preparations is <5000 ppm (in each case based on the PGM content).

18. The process as claimed in claim 1 which further comprises replacement of the OH anions (OH⁻)ₑ in the PGM complexes of the general formulae

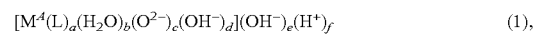    (1),

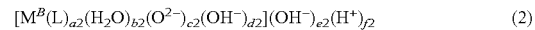    (2)

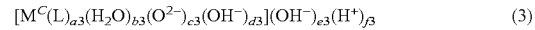    (3)

by one or more anions of inorganic or organic acids (where the meanings of $M^A$, $M^B$, $M^C$, L, a, b, c, d, e, f, a2, b2, c2, d2, e2, f2, a3, b3, c3, d3, e3, and f3 are as defined in claim 1 and e, e2 and e3≠0).

19. The process as claimed in claim 18, wherein the anions of inorganic or organic acids are acetates, formates, oxalates, carbonates, hydrogencarbonates, sulfates, nitrates, phosphates, tetrafluoroborates or mixtures thereof.

20. A process for producing water-containing preparations of complexes of the platinum group metals (PGM) having the general formula (1), (2) or (3)

    (1)

where
$M^A$=platinum (Pt) or palladium (Pd) in the oxidation state +2 and
L=an uncharged monodentate ligand or a bidentate donor ligand wherein the monodenate ligand is ammonia or ligands selected from the group consisting of monoalkylamines, dialkylamines, trialkylamines, monoalkanolamines, dialkanolamines, trialkanolamines, monoarylamines, diarylamines, triarylamines, trialkylphosphines, triarylphosphines, trialkoxyphosphines, triaryloxyphosphines and mixtures thereof or bidentate donor ligand and
a=an integer from 1 to 4 (for monodentate donor ligands) or an integer from 1 to 2 (for bidentate donor ligands),
b=an integer from 0 to 3,
c=an integer from 0 to 3,
d=an integer from 0 to 3,
e=an integer from 0 to 2 and
f=an integer from 0 to 4
and the platinum group metal $M^A$ has the coordination number 4,
wherein the hydroxo complexes H₂Pd(OH)₄ (in the case of $M^A$=Pd) or H₂Pt(OH)₆ (in the case of $M^A$=Pt) are in each case reacted with an uncharged donor ligand L, where at least one hydroxo group of the hydroxo complex concerned is replaced and in the case of $M^A$=Pt the reaction is carried out in the presence of a reducing agent or

  (2)

where $M^B$=platinum (Pt) in the oxidation state +4 and
L=is defined above and
a2=an integer from 1 to 6 (for monodentate donor ligands) or an integer from 1 to 3 (for bidentate donor ligands),
b2=an integer from 0 to 5,
c2=an integer from 0 to 4,
d2=an integer from 0 to 5,
e2=an integer from 0 to 4 and
f2=an integer from 0 to 4
and the platinum group metal $M^B$ has the coordination number 6,
wherein the hydroxo complex $H_2Pt(OH)_6$ is reacted with an uncharged donor ligand L, where at least one hydroxo group of the hydroxo complex is replaced or

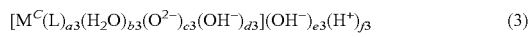  (3)

where $M^C$=rhodium (Rh) or iridium (Ir) in the oxidation state +3 and
L=is defined above and
a3=an integer from 1 to 6 (for monodentate donor ligands) or an integer from 1 to 3 (for bidentate donor ligands),
b3=an integer from 0 to 5,
c3=an integer from 0 to 4,
d3=an integer from 0 to 5,
e3=an integer from 0 to 3 and
f3=an integer from 0 to 5
and the platinum group metal $M^C$ has the coordination number 6,
wherein a hydroxo complex of the type $H_3M^C(OH)_6$ is reacted with an uncharged donor ligand L, where at least one hydroxo group of the hydroxo complex is replaced.

21. A process for producing water-containing preparations of complexes of the platinum group metals (PGM) having the general formula (1), (2) or (3)

  (1)

where $M^A$=platinum (Pt) or palladium (Pd) in the oxidation state +2 and
L=bidentate donor ligand, said bidentate donor ligand is alkylenediamine, arylenediamine, alkylenediphosphine, arylenediphosphine or mixtures thereof, and
a=an integer from 1 to 2 (for bidentate donor ligands),
b=an integer from 0 to 3,
c=an integer from 0 to 3,
d=an integer from 0 to 3,
e=an integer from 0 to 2 and
f=an integer from 0 to 4
and the platinum group metal $M^A$ has the coordination number 4,
wherein the hydroxo complexes $H_2Pd(OH)_4$ (in the case of $M^A$=Pd) or $H_2Pt(OH)_6$ (in the case of $M^A$=Pt) are in each case reacted with an uncharged donor ligand L, where at least one hydroxo group of the hydroxo complex concerned is replaced and in the case of $M^A$=Pt the reaction is carried out in the presence of a reducing agent or

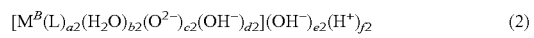  (2)

where $M^B$=platinum (Pt) in the oxidation state +4 and
L=defined above and
a2=an integer from 1 to 6 (for monodentate donor ligands) or an integer from 1 to 3 (for bidentate donor ligands),
b2=an integer from 0 to 5,
c2=an integer from 0 to 4,
d2=an integer from 0 to 5,
e2=an integer from 0 to 4 and
f2=an integer from 0 to 4
and the platinum group metal $M^B$ has the coordination number 6,
wherein the hydroxo complex $H_2Pt(OH)_6$ is reacted with an uncharged donor ligand L, where at least one hydroxo group of the hydroxo complex is replaced or

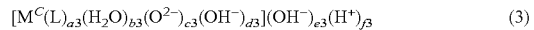  (3)

where $M^C$=rhodium (Rh) or iridium (Ir) in the oxidation state +3 and
L=defined above and
a3=an integer from 1 to 6 (for monodentate donor ligands) or an integer from 1 to 3 (for bidentate donor ligands),
b3=an integer from 0 to 5,
c3=an integer from 0 to 4,
d3=an integer from 0 to 5,
e3=an integer from 0 to 3 and
f3=an integer from 0 to 5
and the platinum group metal $M^C$ has the coordination number 6,
wherein a hydroxo complex of the type $H_3M^C(OH)_6$ is reacted with an uncharged donor ligand L, where at least one hydroxo group of the hydroxo complex is replaced.

22. The process as claimed in claim 21, wherein the water-containing preparations have a pH in the range of 7 to 14.

23. The process as claimed in claim 1, wherein the water-containing preparations have a pH in the range of 7 to 12.

24. The process as claimed in claim 20, wherein the water-containing preparations have a pH in the range of 5 to 14.

* * * * *